United States Patent [19]

Jones et al.

[11] Patent Number: 4,637,397

[45] Date of Patent: Jan. 20, 1987

[54] TRIPHASIC WAVE DEFIBRILLATION

[75] Inventors: Janice L. Jones; Ronald E. Jones, both of Solon, Ohio

[73] Assignee: Case Western Reserve University, Cleveland, Ohio

[21] Appl. No.: 739,133

[22] Filed: May 30, 1985

[51] Int. Cl.⁴ .............................................. A61N 1/36
[52] U.S. Cl. ................................................ 128/419 D
[58] Field of Search ............. 128/419 D, 419 PG, 421

[56] References Cited

U.S. PATENT DOCUMENTS 3,605,754  9/1971  Jaros et al. ...................... 128/419 D
3,706,313 12/1972  Milani et al. .................... 128/419 D
3,860,009  1/1975  Bell et al. ......................... 128/419 D
4,168,711  9/1979  Cannon et al. ................... 128/419 D
4,255,790  3/1981  Hondeghem ......................... 128/421
4,265,228  5/1981  Zoll ....................................... 128/55
4,349,030  9/1982  Belgard et al. ............... 128/419 PG

FOREIGN PATENT DOCUMENTS 1502847 10/1967 France ............................ 128/419 D

OTHER PUBLICATIONS

J. L. Jones, Ronald E. Jones, et al., Response of Cultured Myocardial Cells to Countershock, etc. (1978).
J. L. Jones, Ronald E. Jones, Postcountershock Fibrillation in Digitalized Myocardial Cells in Vitro (1980).
J. L. Jones, Ronald E. Jones, Determination of Safety Factor for Defibrillator Waveforms, etc. (1982).
J. L. Jones, R. E. Jones, Improved Defibrillator Waveform Safety Factor with Biphasic Waveforms (1983).
Schuder et al., Transthoracic Ventricular Defibrillation in the 100 kg Calf, etc., (1983).
Falk et al., Safety and Efficacy of Noninvasive Cardiac Pacing (1983).

Primary Examiner—William E. Kamm
Assistant Examiner—Mitchell J. Shein
Attorney, Agent, or Firm—Fay, Sharpe, Fagan, Minnich & McKee

[57] ABSTRACT

Method and apparatus for stimulation of cells in arrhythmic myocardial tissues includes depolarizing the cells by application of a first electrical pulse or shock followed by a second electrical pulse having a polarity opposite to the first pulse. Finally, a third pulse having the same polarity as the first pulse is applied to the cells. Specific relationships between the magnitudes and durations of the pulses are advantageously employed for achieving the most desirable stimulation results.

16 Claims, 8 Drawing Figures

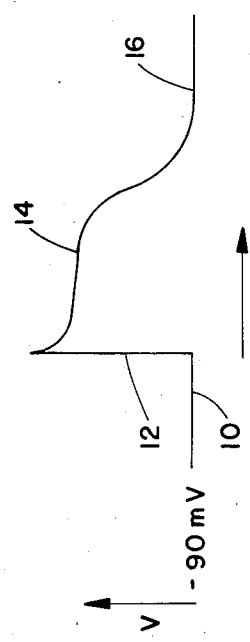
FIG. 1
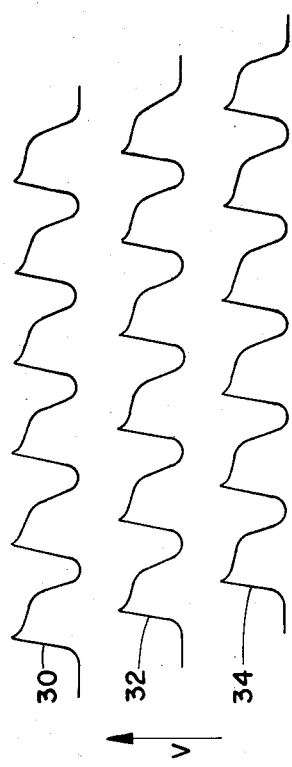
FIG. 3
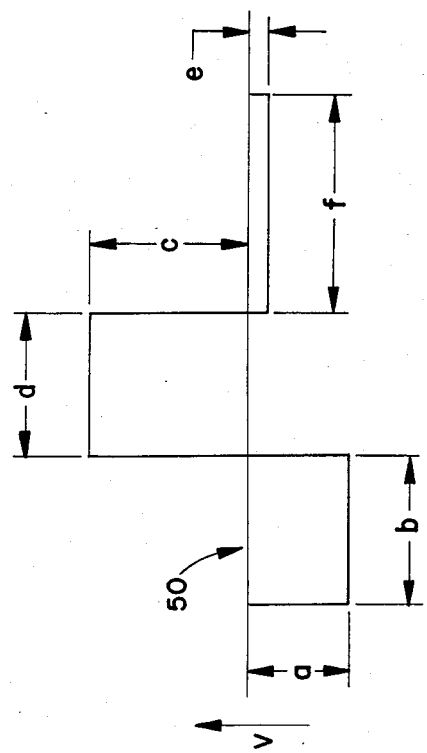
FIG. 4
FIG. 2

TRIPHASIC WAVE DEFIBRILLATION

BACKGROUND OF THE INVENTION

This application relates to the art of medical treatments, and, more particularly, to the application of electrical stimuli to tissues for achieving some desired result.

The invention will be described with particular reference to defibrillation of fibrillating myocardial tissues, and will be described with particular reference thereto. However, it is to be appreciated that the invention has broader applications, and is adapted to other uses and applications. One such other application, for example, is in treatment of tachyarrhythmias.

Electrical stimulation of cells in arrhythmic myocardial tissue has become a well established technique for heart defibrillation. Early waveforms for achieving defibrillation of fibrillating myocardial tissue comprised single voltage pulses in one polarity. The waveshape of these early defibrillators generally comprised a critically dampened RLC form. Though such defibrillation was often successful, it was discovered that several drawbacks were presented with attempted defibrillation through electric stimulation.

If an insufficient voltage were to be applied, the arrhythmia would not be reversed. If too great a voltage were to be applied, refibrillation and other dysfunction may occur. Early critically dampened RLC waveshape defibrillators had a relatively narrow range of voltages with which defibrillation could be accomplished without realizing a large percentage of refibrillation occurrences. A "safety factor" has been defined as the ratio between a voltage producing post-shock dysfunction and a voltage producing cellular excitation. Waveforms with large safety factors defibrillate effectively with little post-shock dysfunction, and waveforms with low safety factors have a low rate of successful defibrillation and produce much postshock dysfunction. Critically dampened RLC waveshapes have a relatively low safety factor. Another type of defibrillator implemented trapezoidal-shaped waves.

Since it has been determined that normal cells have a membrane or resting potential of approximately −90 mV, while cells in arrhythmic myocardial tissues have a resting potential of approximately −60 mV due to a number of factors, e.g., an increase of extracellular potassium and the like, it was concluded that a pre or conditioning pulse of opposite polarity, when applied to cells in arrhythmic myocardial tissues prior to the application of a defibrillating pulse, allowed reactivation of fast excitation channels in the membranes. This produces a substantially lower defibrillation threshold, correspondingly higher safety factor, and a substantially greater chance of defibrillation.

Another modification of defibrillating waveshapes comprises an initial or defibrillating pulse followed by a tail or undershoot pulse of opposite polarity. This waveshape was generally rounded or square in form and was concluded to be of advantage in decreasing the potential for post-shock dysfunction.

While methods and apparatus incorporating various defibrillation and associated pulses have been used with success, it has been considered desirable to improve upon the capabilities of and results obtained from these prior techniques. The subject invention is deemed to meet these needes and others, and provide omre efficient and reliable defibrillation method and apparatus.

SUMMARY OF THE INVENTION

The subject invention provides method and means for stimulation of cells in arrhythmic myocardial tissues by electrical stimulation with a triphasic wave. The method includes applying to the cells a conditioning pulse defined by a predetermined voltage and a predetermined polarity for a predetermined first time period. Subsequent to application of the conditioning pulse, a correcting pulse having a predetermined voltage and a polarity opposite to that of the conditioning pulse is applied for a predetermined second time period. Finally, a healing pulse having a predetermined voltage and a polarity the same as that of the conditioning pulse is applied for a predetermined third time period.

In accordance with another aspect of the invention, the magnitude of the conditioning pulse voltage is generally between 20% and 200% of the correcting pulse voltage. The magnitude of the healing pulse voltage is of a level generally between 5% and 40% of the correcting pulse voltage.

According to a more detailed aspect of the invention, the magnitude of the conditioning pulse voltage is generally between 50% to 100% of the correcting pulse voltage, and the magnitude of the healing pulse voltage is at a level generally between 5% to 20% of the correcting pulse voltage.

In accordance with another aspect of the invention, the conditioning pulse is applied for a time period of between three and fifty milliseconds, the correcting pulse is applied for a time period of between three and fifteen milliseconds, and the healing pulse is applied for a time period of between one and one hundred milliseconds.

According to a more limited aspect of the invention, the duration of the conditioning pulse is generally between ten and forty milliseconds, the duration of the correcting pulse is generally between five and ten milliseconds, and the duration of the healing pulse is generally between ten and fifteen milliseconds.

According to another aspect of the invention, the magnitude of the pulse voltages deteriorates to a level of generally between 50% to 100% of their initial values over their predetermined time periods.

The principal advantage of the present invention resides in the provision of improved method and means for stimulation of cells in arrhythmic myocardial tissues.

Another advantage of the invention resides in providing for an increased range of voltages which may successfully defibrillate or otherwise stimulate fibrillating myocardial tissues with a correspondingly lower chance of refibrillation.

Another advantage is found in a new technique for stimulating cells in arrhythmic myocardial tissues which requires application of lower voltage levels.

Still other advantages and benefits of the invention will become apparent to those skilled in the art upon a reading and understanding of the following detailed specification.

BRIEF DESCRIPTION OF THE DRAWINGS

The invention may take form in certain parts and arrangements of parts, preferred and alternative embodiments of which will be described in detail in the specification and illustrated in the accompanying drawings which form a part hereof and wherein:

FIG. 1 is a graph of the membrane potential of a cell plotted as a function of time;

FIG. 2 is a graph of the membrane potentials of a sampling of cells in normal rhythm;

FIG. 3 is a graph of the membrane potentials of a sampling of arrhythmic cells;

FIG. 4 is a graph of voltage versus time for a triphasic wave formed in accordance with the present invention;

DETAILED DESCRIPTION OF THE PREFERRED AND ALTERNATE EMBODIMENTS

Figure 5:
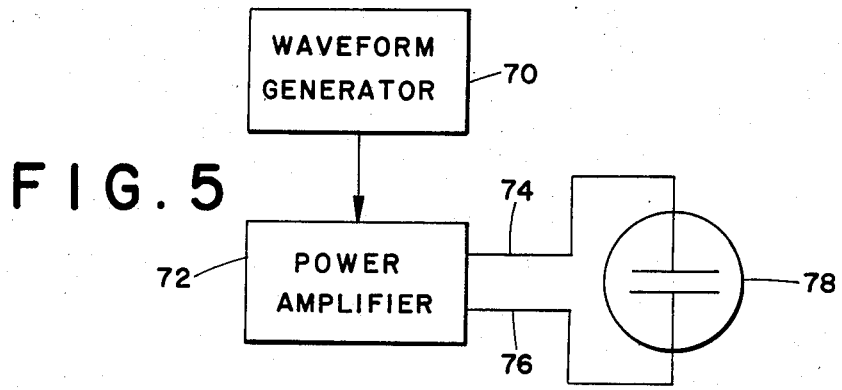
FIG. 5 is a diagram of a circuit for generating the triphasic wave of FIG. 4.

Referring now to the drawings wherein the showings are for purposes of illustrating preferred and alternative embodiments of the invention only, and not for limiting same, FIG. 1 represents graphically the membrane potential of a cell in the cyclic depolarization and repolarization of heart fibers as typically occurs during expansion and contraction of the muscle cells in a beating heart. The voltage V is plotted against time T. When a cell is in a polarized state, its resting potential is approximately −90 mV as illustrated at 10. When at this state, the cell is receptive to electrical stimulation. As a cell is depolarized at 12, the action potential overshoots zero. After depolarization, the cell repolarizes at 14 to its original −90 mV resting potential 16. FIG. 2 is a representation of a group of cells in normal rhythm. It will be noted that depolarization at 20, 22, 24 occurs almost simultaneously for the illustrated cells.

FIG. 3 comprises a sampling of cells in arrhythmic myocardial tissue. During tissue arrhythmia, the various cells of a grouping are depolarized at varied times. This results in an uncoordinated twitching of individual muscular fibers with little or no movement of the muscle as a whole. Such condition is commonly referred to as fibrillation. An appropriate electric shock applied to the cells of fibrillating myocardial tissues will often realign the depolarization periods of FIG. 3 into the synchronous or rhythmic polarization and depolarization of FIG. 2.

FIG. 4 illustrates the novel waveshape for stimulating cells in arrhythmic myocardial tissues contemplated in accordance with the present invention. The waveshape is shown with square-wave components which is preferred for defibrillation; however, it is to be noted that the wave may possess smooth, rather than squared characteristics, and maintain the advantages of the present invention.

An initial pre or conditioning pulse 50 with a polarity −V is applied to the arrhythmic myocardial tissue. This conditioning pulse is defined by a voltage magnitude a and a pulse width b. The voltage magnitude and pulse width are measured relative to a second pulse 56 and will be defined below in relation thereto. The second pulse 56 represents the defibrillating or correcting pulse. A defibrillating pulse comprises a pulse with which normal synchronized depolarization of fibrillating myocardial tissues is accomplished. Defibrillating pulse 56 preferably comprises a square wave having a voltage magnitude c and a pulse width d. A final, healing pulse 60 is applied to the arrhythmic myocardial tissue following application of the defibrillating pulse 56. The healing pulse has a voltage magnitude e and a pulse width f, and is also defined in relation to defibrillating pulse 56.

When the three pulses are applied in the aforenoted manner, it has been found that certain desirable results are realized. Application of the conditioning pulse 50 functions to bring a majority of cells in arrythmic myocardial tissues to their −90 mV resting potential. At this state, the cells are receptive to polarization. Application of the defibrillating pulse 56 restores the cells to simultaneous depolarization and repolarization associated with normal rhythm. Finally, application of the healing pulse 60 results in a reduction in post-shock dysfunction, ie., refibrillation, at defibrillating intensities by aiding in the repair of damage to cell membranes. It has been concluded that the application of the healing pulse 60 serves to counteract the prolonged depolarization of the cell membrane produced by the defibrillating shock at 56.

A variety of pulse widths and magnitudes can be utilized when practicing the present invention. It has been determined that as the pulse width is increased, the intensity of the voltage necessary to accomplish defibrillation may be decreased. Accordingly, the voltage magnitude c and the pulse width d of the defibrillating pulse 56 is chosen according to parameters which can be readily implemented by available equipment and are known to have a maximized defibrillation success rate.

To that end, the width d of the defibrillating pulse was found to be effective when it has a duration of between three and fifteen milliseconds, with optimal results being obtained in the general range of five to ten milliseconds. The conditioning pulse 50 has a pulse width b between three and fifty milliseconds in duration, with optimal results being obtained generally in the range of ten to forty milliseconds. The healing pulse 60 has a pulse width f between one and one hundred milliseconds, with optimal results at a range between ten and fifteen milliseconds. The advantages of the present invention may be realized when magnitude a is between 20% and 200% of the magnitude c, and optimal results are realized with voltage magnitude a generally between 50% and 100% of magnitude c. Similarly, magnitude e is between 5% and 40% of magnitude c, with a voltage level e generally between 5% and 20% of level c being considered optimum. By way of example only, it is expected that defibrillating pulse 56 will be in the general range of 50–400 joules for transthoracic defibrillation, although other values could also be employed.

FIG. 5 represents one means by which the waveshape of FIG. 4 may be achieved. A waveform generator or simulator 70 may be comprised of a programmed digital computer with a low level output proportional to the desired final waveshape. This device includes circuitry capable of delivering any number of waveforms including essentially rectangular waveforms having amplitudes of 0–5 V and durations of 0.1 to 100 milliseconds.

The low level waveshape from generator 70 is fed to a power amplifier 72 which will increase the voltage levels of the waveshape to the desired parameters. A suitable power amplifier can be created from a modified amplifier marketed by Phase-Linear of Lynwood, Washington, and is capable of delivering voltages up to +/−200 V. Two probes or connectors 74, 76 extend from the power amplifier to a means 78 for applying the resultant wave to fibrillating myocardial tissues. Means 78 may comprise any convenient device conventionally used in practicing defibrillation techniques. The relative size and weight of a generator such as that comtemplated in FIG. 5 may be prohibitive for use in a portable unit. Moreover, the illustrated apparatus is merely exemplary, it being appreciated that other apparatus could advantageously be employed without departing from the overall intent or scope of the invention.

Figure 6:
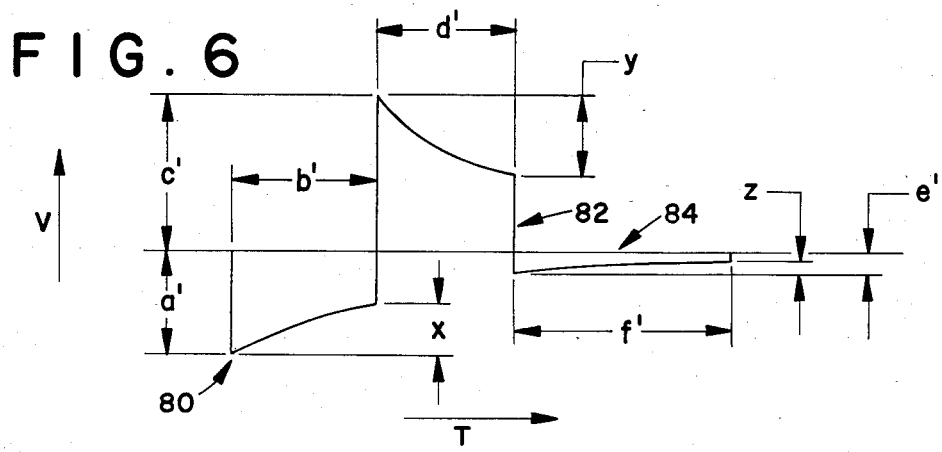
FIG. 6 is a graph of an alternative triphasic wave in accordance with the present invention.

FIG. 6 shows an alternative waveshape which is more conductive to implementation with a portable unit, yet retains the desired characteristic of the subject triphasic defibrillation wave. As with the waveshape of FIG. 4, the alternative triphasic wave includes a pre or conditioning pulse 80 followed by a defibrillating or correcting pulse 82 which is then followed by a healing pulse 84. The defibrillating pulse 82 is of opposite polarity to both the conditioning pulse 80 and the healing pulse 84.

The conditioning pulse 80 includes an initial voltage magnitude a' and a pulse width b'. The defibrillating pulse 82 includes a defibrillating pulse voltage magnitude c' and a defibrillating pulse width d'. The healing pulse 84 includes a healing pulse voltage magnitude e' having a pulse width f'. The relationships between these voltage magnitudes and the time durations thereof are the same as described hereinabove with reference to the waveform of FIG. 4. Therefore, these parameters need not be repeated here.

Unlike the waveshape of FIG. 4, however, the waveshape of FIG. 6 allows for a decrease of the magnitude of the conditioning pulse 80 voltage a' by an amount x of up to 50% of a' over the duration of pulse width b'. Similarly, y denotes an approximate decrease of up to 50% in the magnitude of voltage c' of defibrillating pulse 82 over the duration of defibrillating pulse width d', and z represents an up to 50% reduction of the value of the voltage e' over the duration of pulse width f' of healing pulse 84. At the end of conditioning pulse 80, therefore, a final conditioning pulse voltage of a'−x is presented. Similarly, a final defibrillating pulse voltage of c'−y is present at termination of defibrillating pulse 82, and a final healing pulse voltage with a magnitude of e'−z is resultant at termination of healing pulse 84.

Figure 7:
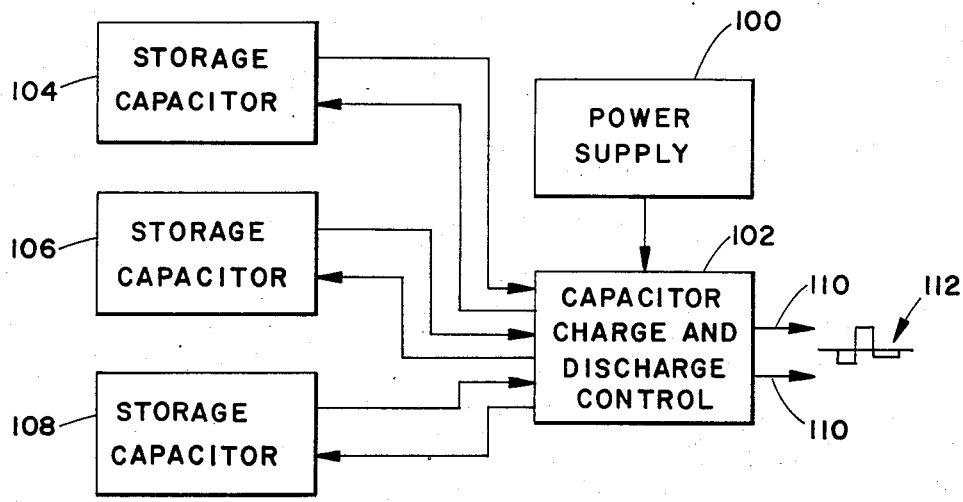
FIG. 7 is a diagram of a circuit for generating the triphasic wave of FIG. 6; and, FIG. 8 is a graph of another alternative triphasic wave in accordance with the present invention.

The modified waveform of FIG. 6 can be generated with an apparatus such as that schematically illustrated in FIG. 7. A power supply 100 is tapped by capacitor charge and discharge control 102 which, in turn, charges storage capacitors 104, 106, 108 to initial voltages a', c' and e', respectively. Upon demand, the capacitor banks 104, 106, 108 can be serially discharged for a predetermined period of time through conventional probes or connectors 110 so that a triphasic wave 112 may be selectively applied to cells in arrhythmic myocardial tissues. As the capacitor banks are discharged over a period of time, their voltages will decrease as depicted by x, y, and z in FIG. 6. The values of capacitors 104, 106, 108 are chosen so as to minimize the voltage decreases or maintain them to at least 50% of their initial voltage at the completion of the duration of their respective periods of application.

As illustrated in FIG. 7, the storage capacitors 104, 106, 108 may be turned on at commencement of their respective pulses, and turned off prior to implementation of the next pulse or at completion of the triphasic wave. Alternately, a subsequent capacitor may be charged to negate the remaining voltage in the capacitor directly preceding it, and negate the necessity for a switching circuit. For example, in FIG. 6 the magnitude c' of the defibrillating pulse would be increased by a magnitude a'−x to allow for a discharge of the remaining voltage in capacitor 104. Similarly, capacitor 108 could be charged by an increased amount of the remaining defibrillating pulse voltage c'−y to counteract the remaining defibrillating pulse voltage. A fourth capacitor bank (not shown) may be charged to a level of the final healing pulse voltage of e'−z to allow for depletion of the remaining charge after healing pulse duration f'. Still other arrangements for achieving the alternate triphasic wave of FIG. 6 are possible without in any way departing from the overall intent and scope of the invention.

Figure 8:
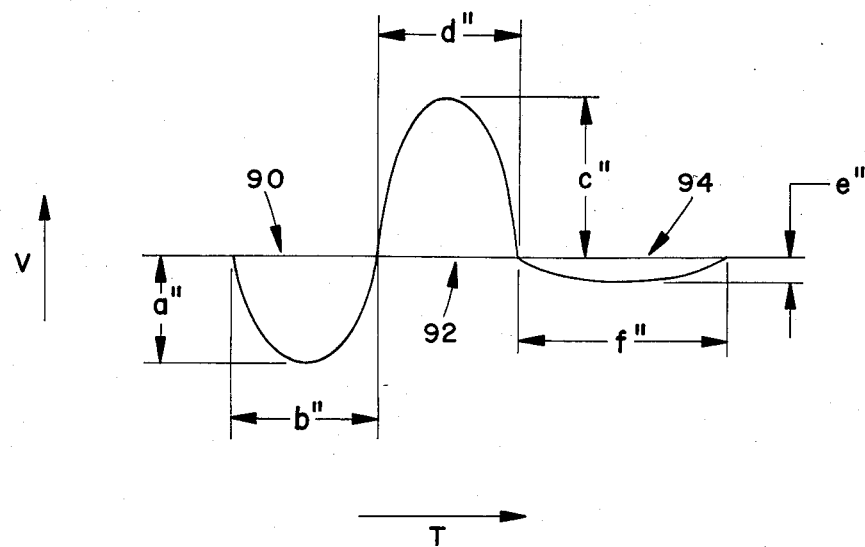

FIG. 8 represents another alternative waveform in accordance with the present invention. This waveform comprises a smooth, RLC-type triphasic wave which similarly presents advantages over the prior art. As with the waveshapes of FIGS. 4 and 6, the RLC-type triphasic wave includes a pre or conditioning pulse 90, a defibrillating or correcting pulse 92, and a healing pulse 94.

The conditioning pulse 90 is parabolic or dampened exponential with a peak voltage a" and a pulse width b". The defibrillating pulse 92 is parabolic with a peak voltage c" and a pulse width d". The healing pulse 94 is similarly parabolic, having a peak voltage e" and a pulse width f". In this alternative embodiment, peak voltages a", c", and e" have the same relationships as voltage magnitudes a, c, and e described in detail above. In like manner, pulse widths b", d", and f" correspond with pulse widths b, d, and f as also described above.

Regarding the waveforms shown and described with reference to FIGS. 4, 6, and 8, it may be possible and/or desirable to include short time intervals between application of the conditioning and defibrillating pulses and between application of the defibrillating and healing pulses. These time intervals may be on the order of magnitude of generally from zero to five milliseconds. Use of such time intervals does not in any way depart from the overall intent or scope of the invention.

Another use of the concepts of the subject invention resides in treatment of a condition referred to as tachyarrhythmia. In this condition, the myocardial tissues are not in a condition of fibrillation. In order to overcome the arrhythmic condition, the myocardial tissues involved are subjected to a triphasic wave in the same manner described above with regard to fibrillating tissues. Here, however, use of a defibrillating and defibrillation pulse is replaced by an excitation or terminating pulse. The same parameters for the triphasic wave described above are also generally applicable to use for treating tachyarrhythmias. However, and as used herein, the term correcting pulse is deemed to be generic to treating fibrillating myocardial tissues or tissues in a condition of tachyarrhythmia.

The invention has been described with reference to preferred and alternate embodiments. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. A method for electrical defibrillation of fibrillating myocardial tissues comprising the steps of:
   (a) defining a defibrillating pulse with a defibrillating polarity, a defibrillating voltage, and a defibrillating pulse width between three and fifteen milliseconds in duration;
(b) defining a conditioning pulse with a polarity opposite to the defibrillating polarity, a conditioning pulse voltage level between 20% and 200% of the defibrillating voltage, and a conditioning pulse width between three and fifty milliseconds in duration;
(c) defining a healing pulse with the opposite polarity as the defibrillating polarity, a healing pulse voltage level between 5% and 40% of the defibrillating voltage, and a healing pulse width between one and one-hundred milliseconds in duration; and,
(d) applying the conditioning pulse, the defibrillating pulse, and the healing pulse in sequence to cells in said fabrillating myocardial tissues.

2. The method for defibrillation of claim 1 wherein the conditioning pulse, the defibrillating pulse, and the healing pulse voltages decrease over their respective pulse widths to final pulse voltages generally between 50% and 100% of their initial voltages.

3. The method for defibrillation of claim 1 wherein said steps of defining conditioning and healing pulses comprises said conditioning pulse voltage being 50% to 100% of said defibrillating pulse voltage and said healing pulse voltage being 5% to 20% of said defibrillating pulse voltage.

4. The method of defibrillation of claim wherein said steps of defining defibrillating, conditioning, and healing pulses comprises adjusting said defibrillating pulse width to be between five and ten milliseconds in duration, said conditioning pulse width to be between ten and forty milliseconds in duration, and said healing pulse to be between ten and fifteen milliseconds in duration.

5. A method for electrically stimulating cells in arrhythmic myocardial tissues, said method comprising the steps of:
(a) defining a conditioning pulse with a conditioning pulse time period, a conditioning pulse voltage, and a conditioning pulse polarity;
(b) defining a correcting pulse with a correcting pulse time period, and a correcting pulse voltage with a polarity opposite to that of said conditioning pulse voltage;
(c) defining a healing pulse with a healing pulse time period, and a healing pulse voltage with the same polarity as said conditioning pulse voltage; and
(d) applying the conditioning pulse, the correcting pulse, and the healing pulse in sequence to said cells in arrhythmic myocardial tissues.

6. The method for stimulating of claim 5 including the steps of establishing the correcting pulse voltage prior to the step of applying the conditioning pulse, and defining the conditioning pulse voltage at a level between 20% and 200% of the correcting pulse voltage and the healing pulse voltage at a level between 5% and 40% of the correcting pulse voltage.

7. The method for stimulating of claim 6 wherein the step of defining comprises having the conditioning pulse voltage be at a level between 50% and 100% of the correcting pulse voltage and the healing pulse voltage be at a level between 5% and 20% of the correcting pulse voltage.

8. The method for stimulating of claim 5 including the step of determining said conditioning and healing pulse voltages by using voltages which comprise percentage values of said predetermined correcting pulse voltage.

9. The method for stimulating of claim 8 further including the step of maintaining the conditioning pulse between three and fifty milliseconds, the correcting pulse between three and fifteen milliseconds, and the healing pulse between one and one hundred milliseconds.

10. The method for stimulating of claim 9 wherein said step of maintaining comprises setting the conditioning pulse to extend between ten and forty milliseconds, the correcting pulse to extend between five and ten milliseconds, and the healing pulse to extend between ten and fifteen milliseconds.

11. A method for stimulating of claim 5 including the steps of allowing each of said conditioning, correcting, and healing pulse voltages to decrease from their respective predetermined voltages over their respective time periods to final voltages.

12. The method for stimulating of claim 11 wherein said step of allowing comprises having said conditioning, correcting, and healing pulse final voltages equal to between 50% to 100% of their respective predetermined voltages.

13. A defibrillator device comprising:
means for generating a triphasic electrical wave including a conditioning pulse with a conditioning pulse polarity, a defibrillating pulse with a defibrillating pulse polarity opposite to the conditioning pulse polarity, and a healing pulse with a healing pulse polarity the same as the conditioning pulse polarity; and,
means for selectively applying the triphasic wave to cells in arrhythmic myocardial tissues.

14. The defibrillator device of claim 13 including means for controlling the widths of said conditioning, defibrillating, and healing pulses, whereby the conditioning pulse may have a width between ten and forty milliseconds in duration, the defibrillating pulse may have a width between five and ten milliseconds in duration, and the healing pulse may have a width between one and one-hundred milliseconds in duration.

15. The defibrillator of claim 13 wherein said generating means includes means for providing said defibrillating pulse with a predetermined defibrillating pulse voltage, said conditioning pulse with a voltage between 20% and 200% of the defibrillating pulse voltage and said healing pulse with a voltage between 5% and 40% of the defibrillating pulse voltage.

16. The defibrillator of claim 15 wherein said generating means includes means for allowing the conditioning, defibrillation, and healing pulse voltages to decrease over their respective pulse widths to final voltages between 50% and 100% of their initial voltages.

* * * * *